(12) United States Patent
Kuriyama et al.

(10) Patent No.: US 6,800,257 B1
(45) Date of Patent: Oct. 5, 2004

(54) PROCESS FOR PREPARING TRICHLORACETIC ACID AND APPARATUS FOR USE IN SUCH PROCESS

(75) Inventors: Akira Kuriyama, Atsugi (JP); Etsuko Sugawa, Atsugi (JP); Kinya Kato, Atsugi (JP); Masahiro Kawaguchi, Atsugi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/685,740

(22) Filed: Oct. 11, 2000

(30) Foreign Application Priority Data

Oct. 12, 1999 (JP) ............................................ 11-289770

(51) Int. Cl.[7] .................................................. B01J 9/12
(52) U.S. Cl. ................... 422/186.3; 210/748; 210/750; 210/806; 210/150; 210/188; 210/192
(58) Field of Search ....................... 422/186.3; 210/748, 210/750, 806, 150, 188, 192; 204/157.8, 554, 232

(56) References Cited

U.S. PATENT DOCUMENTS

| | | | | |
|---|---|---|---|---|
| 4,144,152 A | * | 3/1979 | Kitchens .................... | 204/158 |
| 4,144,162 A | * | 3/1979 | Edgar et al. ............... | 204/158 |
| 4,452,678 A | * | 6/1984 | Ollivier ................. | 204/158.14 |
| 4,761,208 A | * | 8/1988 | Gram et al. ................. | 204/95 |
| 5,094,815 A | * | 3/1992 | Conboy et al. .............. | 422/52 |
| 5,308,507 A | * | 5/1994 | Robson ...................... | 210/748 |
| 5,478,481 A | * | 12/1995 | Kazama et al. ............. | 210/748 |
| 5,578,193 A | * | 11/1996 | Aoki et al. ................. | 205/746 |
| 5,779,912 A | * | 7/1998 | Gonzalez-Martin et al. | 210/748 |

FOREIGN PATENT DOCUMENTS

| | | |
|---|---|---|
| EP | 0 968 739 A1 | 1/2000 |
| EP | 1 005 881 A1 | 6/2000 |
| JP | 37-4111 | 6/1937 |
| JP | 39-2135 | 3/1939 |
| JP | 1-180293 | 7/1989 |
| JP | 5-178786 | 7/1993 |
| JP | 7-51675 | 2/1995 |
| JP | 02000084357 * | 3/2000 ........... B01D/53/70 |

OTHER PUBLICATIONS

I.V. Dobrov et al., "Radiation–Chemical Synthesis of Trichloroacetic Acid," 2 *Radiats. Khim.* 131–137 (1972) (Abstract).

European Search Report in Application No. 00122084.7 (Dec. 2, 2002).

* cited by examiner

Primary Examiner—James J. Seidleck
Assistant Examiner—Thao Tran
(74) Attorney, Agent, or Firm—Fitzpatrick, Cella, Harper & Scinto

(57) ABSTRACT

A process for preparing trichloroacetic acid comprises the step of bringing functional water capable of partial oxidizing tetrachloroethylene under irradiation with light or aerated functional water gas which is produced by aerating the above functional water and has a capability similar to that of the above functional water into contact with tetrachloroethylene under irradiation with light. And an apparatus for preparing trichloroacetic acid comprises a closable container as a means for bringing functional water capable of partial oxidizing tetrachloroethylene under irradiation with light or aerated functional water gas which is produced by aerating the above functional water and has a capability similar to that of the above functional water into contact with tetrachloroethylene, and means for irradiating the above contact mixture with light.

12 Claims, 1 Drawing Sheet

FIGURE
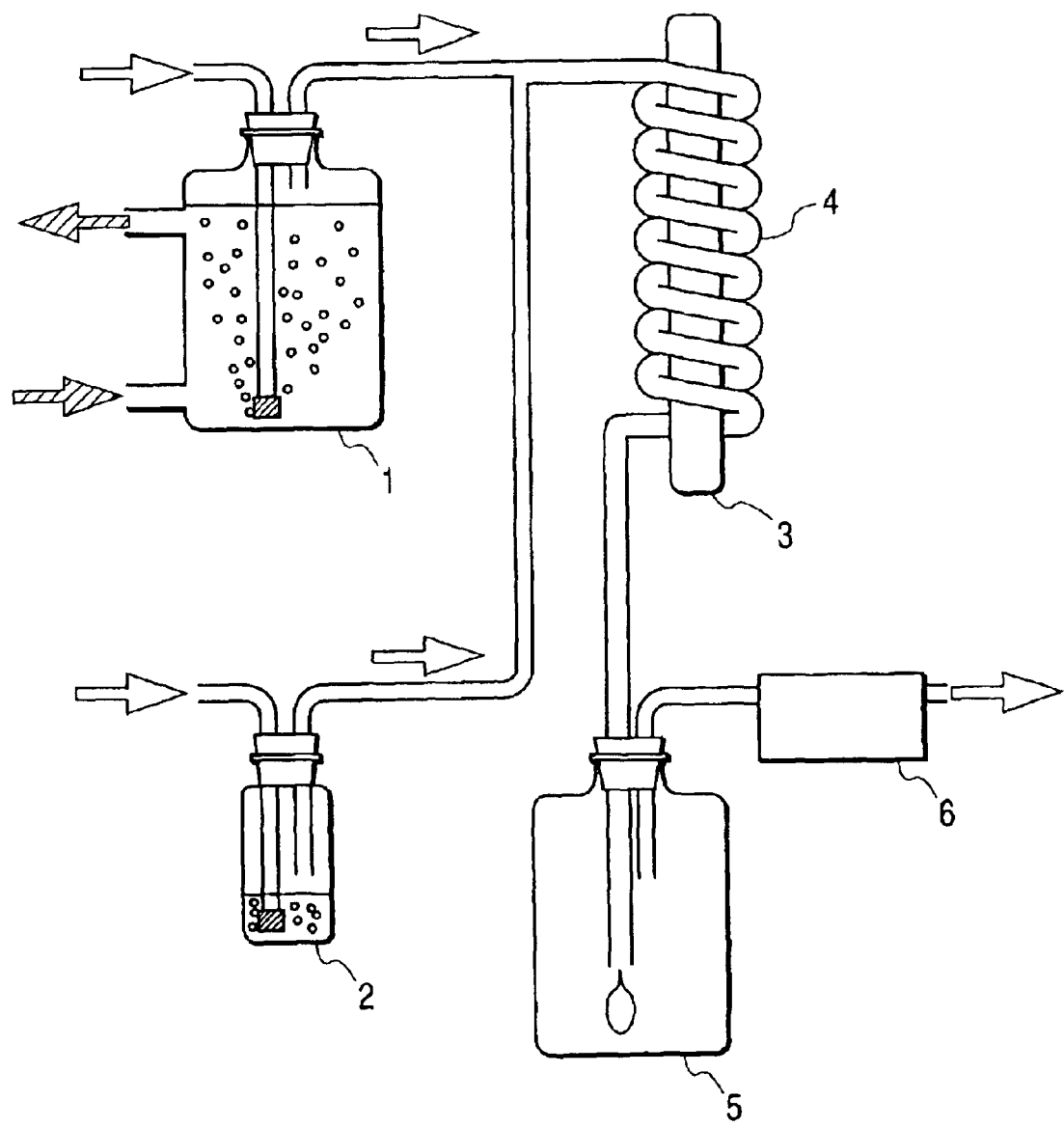

PROCESS FOR PREPARING TRICHLORACETIC ACID AND APPARATUS FOR USE IN SUCH PROCESS

BACKGROUND OF THE INVENTION

1. Field of the Invention

The present invention relates to a process for preparing trichloroacetic acid from tetrachloroethylene using functional water under irradiation with light and an apparatus for use in such process.

2. Related Background Art

Trichloroacetic acid is a useful compound which is not only used as a raw material for pharmaceuticals, herbicides, caustics, paint removers and deproteinizing agents, but also used for extracting ATP and AMP and separating DNA from protein.

There have been known various processes for preparing trichloroacetic acid. Such processes include, for example, oxidizing chloral with nitric acid, organic percarboxylic acid, hydrogen peroxide, etc.; chlorinating acetic acid, monochloroacetic acid or dichloroacetic acid (Japanese Patent Publication No. 37-4111); hydrolyzing trichloroacetonitrile with hydrochloric acid (Japanese Patent Publication No. 39-2135); hydrolyzing trichloroacetyl chloride; and oxidizing chloral with nitric acid. In particular, Japanese Patent Application Laid-Open No. 5-178786 discloses a process for oxidizing chloral with nitric acid to prepare trichloroacetic acid in which the NO gas produced is oxidized into $NO_2$ in a reactor and condensed, so as to be recycled.

As industrial processes, chlorinating dichloroacetic acid which is produced as a by-product in manufacturing monochloroacetic acid and oxidizing chloral with nitric acid are adopted.

In the industrial processes as described above, however, the reactions require a high temperature and take a long period time. In addition, in the process for oxidizing chloral with nitric acid, a number of processes and a large amount of chemical agents are required for detoxifying a large amount of $NO_2$ and NO gases produced during the oxidation process. Under these circumstances, there have been demands for developing some other process for preparing trichloroacetic acid.

In light of the existing circumstances as described above, the present inventors conducted an intensive investigation of the processes and finally found the fact that functional water such as acidic water obtained by electrolysis of water, which has been reported to have a bactericidal effect (Japanese Patent Application Laid-Open No. 1-180293) and a cleaning effect on the contaminations on semiconductor wafers (Japanese Patent Application Laid-Open No. 7-051675), decomposes tetrachloroethylene into trichloroacetic acid at ordinary temperature and normal pressure in a short time when irradiating it with light. The present invention has been thus achieved.

Tetrachloroethylene used in the present invention as a raw material was once widely and abundantly used in various industries as cleaning solvents for metal parts, semiconductor devices, clothing, etc. and as reactive solvents as well, just like trichloroethylene. However, since the time of the toxicity of these compounds, such as mutagenicity and carcinogenicity, to organisms having been pointed out, there have been strong demands that those stored without having been used and those having leaked out in nature be treated. Viewed in this light, and moreover, in terms of transforming disused articles into useful ones, the present invention is considered to be of great significance.

SUMMARY OF THE INVENTION

The present invention is a process for preparing trichloroacetic acid comprising the step of bringing functional water capable of partial oxidizing tetrachloroethylene under irradiation with light or aerated functional water gas which is produced by aerating the above functional water and has a capability similar to that of the above functional water into contact with tetrachloroethylene under irradiation with light.

Further, the present invention is an apparatus for preparing trichloroacetic acid comprising a closable container as a means for bringing functional water capable of partial oxidizing tetrachloroethylene under irradiation with light or aerated functional water gas which is produced by aerating the above functional water and has the capability similar to that of the above functional water into contact with tetrachloroethylene; and means for irradiating the above contact mixture with light.

According to the present invention, trichloroacetic acid can be prepared by the process in which tetrachloroethylene, which is one of the causes of groundwater contamination and soil contamination, is brought into contact with aerated functional water gas at ordinary room temperature and normal pressure under irradiation with light, instead of the prior art processes such as chlorinating dichloroacetic acid at a high temperature for a long period of time and oxidizing chloral with nitric acid in which a number of processes and a large amount of chemical agents are required for detoxifying a large amount of $NO_2$ and NO gases produced.

In other words, according to the present invention, trichloroacetic acid, which is used for the preparation of pharmaceuticals, chemical agents, etc., can be prepared using the compounds which was once contaminants of no utility value as raw materials.

BRIEF DESCRIPTION OF THE DRAWINGS

FIGURE shows an apparatus for continuously preparing trichloroacetic acid with aerated functional water gas, which is for use in the present invention.

DETAILED DESCRIPTION OF THE PREFERRED EMBODIMENTS

As described above, the present invention is a process for preparing trichloroacetic acid comprising the step of bringing functional water capable of partial oxidizing tetrachloroethylene under irradiation with light or aerated functional water gas which is produced by aerating the above functional water and has the capability similar to that of the above functional water into contact with tetrachloroethylene under irradiation with light.

Further, the present invention is an apparatus for preparing trichloroacetic acid comprising a closable container as a means for bringing functional water capable of partial oxidizing tetrachloroethylene under irradiation with light or aerated functional water gas which is produced by aerating the above functional water and has a capability similar to that of the above functional water into contact with tetrachloroethylene; and means for irradiating the above contact mixture with light.

(Functional Water—Acid Electrolytic Ionized Water)

The functional water produced by electrolyzing water means, for example, water which can be obtained near an anode by dissolving an electrolyte (such as sodium chloride and potassium chloride) in raw water and electrolyzing the water in a water bath with a pair of electrodes and which has the following properties: a hydrogen ion concentration (pH value) ranging from 1 to 4, an oxidation-reduction potential ranging from 800 mV to 1500 mV when the working electrode is a platinum electrode and a reference electrode is a silver—silver chloride electrode, and a chlorine concentration ranging from 5 mg/L to 150 mg/L.

When producing functional water having the properties described above, the concentration of the electrolyte in the raw water is desirably 20 mg/L to 2000 mg/L before electrolysis and the electrolytic current value is desirably 2 A to 20 A. As a means for obtaining such functional water, commercially available strong acid electrolytic ionized water production equipment (for example, trade name: Oasis Bio Half; manufactured by Asahi Glass Engineering Co., Ltd., trade name: Strong Electrolytic Ionized Water Production Equipment Model FW-200; manufactured by Amano Corporation) can be utilized.

In the production of functional water, arranging a diaphragm between a pair of electrodes allows the prevention of acidic water produced near an anode and alkaline water produced near a cathode from mixing with each other, thereby acidic water can be obtained which ensures more efficient preparation of trichloroacetic acid. As the diaphragm as described above, for example, an ion-exchange membrane, a micro-porous membrane or the like is suitably used.

(Functional Water—Mixed Electrolytic Ionized Water)

In addition to the acid electrolytic ionized water as described above, the mixed electrolytic ionized water which is obtained by mixing acidic water and alkaline water obtained near a cathode in the electrolysis to produce the acid electrolytic ionized water, in the ratio of 1:1 or less and which has the following properties: the hydrogen ion concentration (pH value) ranging from 4.0 to 10, the oxidation-reduction potential ranging from 300 mV to 1100 mV when the working electrode is a platinum electrode and the reference electrode is a silver—silver chloride electrode, and the chlorine concentration ranging from 2 mg/L to 100 mg/L has the same synthesis power as the acid electrolytic ionized water.

(Functional Water—Synthesized Functional Water)

The functional water having almost the same tetrachloroethylene-decomposition power as the above-described functional water produced by electrolysis can also be prepared not only by electrolysis, but also by dissolving various reagents in raw water. For example, such functional water can be obtained by dissolving in raw water 0.001 to 0.1 N hydrochloric acid, 0.005 to 0.02 N sodium chloride and 0.0001 to 0.01 M sodium hypochlorite.

Further, the functional water having a pH value ranging from 4.0 to 10 can also be obtained not only by the electrolysis, but also by dissolving various reagents in raw water. For example, such functional water can be obtained with hydrochloric acid at a concentration of 0.001 to 0.1 N, sodium hydroxide at a concentration of 0.001 to 0.1 N and sodium hypochlorite at a concentration of 0.0001 to 0.01 M, or with hypochlorite alone, for example with sodium hypochlorite at a concentration of 0.0001 to 0.01 M, alone.

The functional water having a pH value of 4.0 or less and a chlorine concentration of 2 mg/L can be prepared with hydrochloric acid and hypochlorite. Instead of hydrochloric acid as described above, some other inorganic acid or organic acid can also be used. The inorganic acids applicable include, for example, hydrofluoric acid, sulfuric acid, phosphoric acid and boric acid. The organic acids applicable include, for example, acetic acid, formic acid, malic acid, citric acid and oxalic acid. Further, functional water can also be produced with a weak acidic water producing powdered agent (for example, $N_3C_3O_3NaCl_2$ commercially available under the trade name of Kinosan 21X; manufacture by Clean Chemical Co., Ltd.).

The functional water prepared by the above-described chemical compounding also has the capability of synthesizing trichloroacetic acid when irradiated with light, like the functional water prepared by the electrolysis, though there is a difference in the synthesis power between the two, as seen from the examples described later. The raw water herein used include, for example, tap water, river water and seawater. These types of water usually have a pH value ranging from 6 to 8 and a chlorine concentration less than 1 mg/L at the most. It goes without saying that these types of raw water have neither tetrachloroethylene-decomposition power nor trichloroacetic acid-synthesis power.

(Aerated Functional Water Gas)

The aerated functional water gas means the gas obtained by aerating the above-described acid electrolytic ionized water, mixed electrolytic ionized water and synthesized functional water in oxygen gas or a gaseous mixture of oxygen gas and an inert gas. The gaseous mixture of oxygen gas and an inert gas is not limited to a specific one, and even when using air as a gaseous mixture, trichloroacetic acid of quality adequate for use in the ordinary applications can be obtained. In order to obtain trichloroacetic acid of higher purity, oxygen gas should be used solely, or when using a gaseous mixture of oxygen gas and an inert gas, any one of the rare gases such as helium, neon and argon should be used as an inert gas. In this case, the higher the purity of the oxygen gas used is, the more preferable the product is.

The aerated functional water gas contains chlorine gas, steam and oxygen. The chlorine concentration is preferably 5 to 1000 ppm V, particularly preferably 20 to 500 ppm V. The steam is the moisture mixed with the gas when aerating the functional water. Its concentration does not need to be controlled; rather, it should not be controlled, because, if the temperature of the functional water is raised intentionally to a temperature higher than room temperature, so as to increase the steam amount, the purity of the trichloroacetic acid prepared is lowered due to the moisture condensation occurring within the tetrachloroethylene reactor. As for oxygen concentration, not less than 10% is enough, and it does not need to be raised to a concentration higher than that of air.

(Tetrachloroethylene)

The tetrachloroethylene used as a raw material for trichloroacetic acid may be that prepared solely for industrial use. However the tetrachloroethylene may also be used such that it was once used at factories etc. for, for example, cleaning metal parts, semiconductor devices, clothing, etc., leaked in nature, contaminated river water, underground water and soil, and recovered therefrom afterward by the vacuum suction of soil or the aeration of underground water. The higher the purity of tetrachloroethylene is, the more preferable the product is.

(Light Source)

For the light used in the preparation of trichloroacetic acid with functional water for irradiating purpose, its wavelength is preferably 300 to 500 nm, particularly preferably 350 to 450 nm. The intensity of the light irradiating various types of functional water or aerated functional water gas and tetrachloroethylene as a raw material is preferably 10 $\mu W/cm^2$ to 10 $mW/cm^2$, particularly preferably 50 $\mu W/cm^2$ to 5 mW/cm$^2$, in terms of synthetic efficiency. Specifically, for the light source having the peak at a wavelength of 365 nm, a good enough amount of synthesis progresses with the intensity of several hundreds $\mu$W/cm$^2$ (measured at the wave lengths between 300 nm to 400 nm).

As a source of the light as described above, natural light (such as sunlight) or artificial light (mercury lamp, black light, color fluorescent lamp, etc.) can be used.

In order to accelerate the synthesis, light irradiation is conducted preferably at the time various types of functional water or aerated functional water gas and tetrachloroethylene are allowed to come in contact with each other. In the embodiments of the present invention where functional water is used, it is not necessary to use ultraviolet light with a wavelength of 250 nm which affects the human body significantly.

All the reactions of the various types of functional water and aerated functional water gas described above progress under irradiation with light. In such reactions, the functional water produced by, for example, the electrolysis of the water containing an electrolyte such as sodium chloride contains hypochlorous acid or hypochlorous acid ions. And it is considered that these hypochlorous acid or hypochlorous acid ions induce chlorine radicals, hydroxyl radicals and superoxide anions with the aid of the light action, leading to accelerating the reaction of producing trichloroacetic acid.

The amount of the hypochlorous acid, which is considered to contribute to the production of trichloroacetic acid, in the functional water produced near an anode by the electrolysis thereof can be obtained based on the PH value and the chlorine concentration of the functional water. The water obtained by diluting the functional water with deionized water etc. can also be used for the production of trichloroacetic acid.

A process of preparing trichloroacetic acid with functional water will be described below. In the embodiments of the present invention, the process of allowing tetrachloroethylene and functional water or aerated functional water gas to come in contact with each under light irradiation can be carried out at the ordinary room temperature and normal pressure. Accordingly there is no need for special facilities and environment.

The processes in which functional water itself is allowed to contact with tetrachloroethylene include, for example, directly mixing the above two; and conducting electrolysis in an electrolytic bath containing an aqueous electrolyte with tetrachloroethylene added thereto.

Preparing trichloroacetic acid by these processes is simple and easy, but on the other hand, there may be cases where water, electrolyte in functional water, etc. mix with the trichloroacetic acid prepared as impurities. Thus, in order to avoid allowing those impurities to mix with the trichloroacetic acid prepared, the process is more preferable in which functional water itself is not allowed to contact with tetrachloroethylene, but the functional water gas, which is obtained by aerating the functional water previously prepared or the functional water being prepared in the electrolysis with oxygen gas or a gaseous mixture of oxygen gas and an inert gas, is allowed to contact with tetrachloroethylene.

The process of the present invention may be carried out in accordance with any one of the batch method and the continuous method. When adopting the batch method, tetrachloroethylene and functional water or aerated functional water gas may be filled into a glass container at a time and irradiated with light. When adopting the continuous method, an apparatus, for example, shown in FIGURE may be used.

The aerated functional water gas is supplied by aerating the functional water in a functional water aerating bath 1 with compressed air. This functional water aerating bath may also be allowed to serve as an electrolytic bath by providing the bath with electrodes and a diaphragm for separating the electrolysis solution between the electrodes and arranging a bubbler for the aeration near the anode.

Tetrachloroethylene, as the raw material, is vaporized by being aerated with oxygen gas or a gaseous mixture of oxygen gas and an inert gas, such as air, sent to a bubbler arranged in a tetrachloroethylene vaporizing bath 2.

The aerated functional water gas and the vaporized tetrachloroethylene are mixed with each other and allowed to pass through a reaction coil 4 made of glass tube which goes down in the direction of gravity while winding around a light irradiating means 3, so as to produce trichloroacetic acid. The trichloroacetic acid produced within the reaction coil 4, which is in the liquid state, is pushed by the gas within the glass tube coil due to the heat of the light irradiating means 3 and allowed to drop into a recovery bath 5. In the recovery bath, the trichloroacetic acid is cooled, condensed, and finally crystallized.

Although the melting point of trichloroacetic acid is about 57° C., in cases where the calorific power of the light irradiating means 3 is too low and the trichloroacetic acid is condensed, a heater for heating the reaction coil 4 may be prepared specially or the entire reaction apparatus may be heated so as to raise the temperature within the reaction coil 4 to about 60° C. The gas discharged from the coil is introduced into a trap 6 and the excess chlorine gas and hydrogen chloride gas are adsorbed therein, after that, the trap is exhausted.

Hydrogen chloride is considered to be produced during the reaction. However, in the batch method, it is easily volatilized by raising the temperature of the water in a glass bottle which is used in the reaction. In the continuous method, the trichloroacetic acid produced is easy to separate, since it is cooled at room temperature after discharged from the reaction coil, condensed and finally solidified. When intending to heighten the purity of the trichloroacetic acid, the liquid obtained after the reaction should be refined by, for example, the vacuum distillation, the solvent extraction and the adsorption separation.

Now the present invention will be described in further detail based on the examples below.

EXAMPLE 1

Preparation of Batch with Acid Electrolytic Ionized Water

First, functional water was prepared with strong acid functional water production equipment (trade name: Strong Electrolytic Ionized Water Production Equipment; manufactured by Amano Corporation, Model FW-200). In this case, a diaphragm was arranged between the anode and the cathode.

While changing the electrolyte concentration of the water electrolyzed and the electrolysis time using this equipment, the pH values and oxidation-reduction potentials of the acid functional water obtained on the side of the anode in this equipment were measured with a pH meter (TCX-90i and KP900-2N; manufactured by Toko Chemical Institute, Co., Ltd.) and a conductivity meter (TCX-90i and KP900-2N; manufactured by Toko Chemical Institute, Co., Ltd.), respectively, and the chlorine concentration of the same was measured with chlorine test paper (Advantic Co., Ltd.).

As a result, the pH value, the oxidation-reduction potential and the chlorine concentration of this functional water varied from 1.0 to 4.0, from 800 mV to 1500 mV and from 5 mg/L to 150 mg/L, respectively, with the concentration of sodium chloride as the electrolyte (a standard concentration is 1000 mg/L), the electrolytic current value and the electrolysis time. Then in this example, functional water with a pH value of 2.6, an oxidation-reduction potential of 1000 mV and a residual chlorine concentration of 75 mg/L was prepared as functional water used for an experiment of the production of trichloroacetic acid.

2.6 mL of this functional water and 8.2 µL (about 13 mg) of tetrachloroethylene stock solution were put in a 27.5 mL glass vial, and the glass vial was sealed with a butyl rubber stopper with Teflon liner. Then this glass vial was installed in a seesaw type stirrer and was irradiated with light, while stirring the mixed solution, using a black light fluorescent lamp (trade name: FL10BLB; manufactured by Toshiba Corporation, 10 W) installed above the glass vial. The quantity of the irradiating light was 0.1 to 0.2 mW/cm$^2$.

After 60-minute light irradiation, the fluorescent lamp was turned off, the gas in the glass vial was sampled with a gas tight syringe and measured with a gas chromatography (GC-14B with a Fire Ionized Detector; manufactured by Shimadzu Corporation, The column used was DB-624 manufactured by J&W). As a result, no tetrachloroethylene was detected. Then the liquid in the glass vial was sampled and measured with a high pressure liquid chromatography (manufactured by Waters), as a result of which it was found that trichloroacetic acid was produced at a concentration of 4500 mg/L.

After tetrachloroethylene was mixed with the electrolytic functional water and irradiated with light, it was found that trichloroacetic acidic aqueous solution was obtained in a yield of 89% in 60 minutes.

COMPARATIVE EXAMPLE 1

The same experiment as in Example 1 was conducted, except that the black light fluorescent lamp was not turned on. Sixty minutes after mixing the functional water and tetrachloroethylene stock solution, the gas in the glass vial was measured, and 56000 ppm V of tetrachloroethylene was detected. Then the liquid in the glass vial was measured, but no trichloroacetic acid was detected.

Thus, it was found that, even in cases where tetrachloroethylene was mixed with the electrolytic functional water, if the mixed liquid was not irradiated with light, the reaction did not occur and tetrachloroethylene remained as it was.

EXAMPLE 2

Preparation of Batch with Mixed Electrolytic Ionized Water

Electrolysis was conducted with the same electrolytic ionized water production equipment as in Example 1 using sodium chloride with a concentration of 1000 mg/L as the electrolyte, so as to prepare acid functional water with a pH value of 2.6, an oxidation-reduction potential of 1000 mV and a residual chlorine concentration of 70 mg/L on the anode side and alkaline functional water with a pH value of 11.5, an oxidation-reduction potential of 850 mV and a residual chlorine concentration of 10 mg/L on the anode side. The acid functional water and the alkaline functional water were mixed in the ratio of 1:1, so as to prepare mixed functional water a with a pH value of 7.1, an oxidation-reduction potential of 400 mV and a residual chlorine concentration of 42 mg/L. Further, the acid functional water and the alkaline functional water were mixed in the ratio of 1:0.5, so as to prepare mixed functional water b with a pH value of 6.5, an oxidation-reduction potential of 480 mV and a residual chlorine concentration of 47 mg/L. And the same experiment as in Example 1 was conducted, except that these types of functional water were used.

After 60-minute light irradiation, the fluorescent lamp was turned off and the gas in the glass vial was measured. As a result, no tetrachloroethylene was detected for both the functional water a and b. Then the liquid in the glass vial was measured, and it was found that trichloroacetic acid was produced at a concentration of 4100 mg/L for the mixed functional water a and at a concentration of 4200 mg/L for the mixed functional water b.

After tetrachloroethylene was mixed with each mixed functional water and irradiated with light, it was found that trichloroacetic acidic aqueous solution was obtained in a yield of 81% for the mixed functional water a and in a yield of 83% for the mixed functional water b in 60 minutes.

EXAMPLE 3

Preparation of Batch with Synthesized Functional Water

First, the pH value, the oxidation-reduction potential and the chlorine concentration were measured for the aqueous solution prepared to have a hydrochloric acid concentration of 0.001 to 0.1 N, a sodium chloride concentration of 0.005 to 0.02 N and a sodium hypochlorite concentration of 0.0001 to 0.01M. As a result, the pH value varied in the range of 1.0 to 4.0, the oxidation-reduction potential in the range of 800 mV to 1500 mV and the chlorine concentration in the range of 5 mg/L to 150 mg/L.

Then in this example, the aqueous solution was prepared in a glass vial to have a hydrochloric acid concentration of 0.006 N, a sodium chloride concentration of 0.014 N and a sodium hypochlorite concentration of 0.002M, and functional water with a pH value of 2.3, an oxidation-reduction potential of 1180 mV and a residual chlorine concentration of 105 mg/L. The same experiment as in Example 1 was conducted, except that this functional water was used.

After 60-minute light irradiation, the fluorescent lamp was turned off and the gas in the glass vial was measured. As a result, no tetrachloroethylene was detected. Then the liquid in the glass vial was measured, and it was found that trichloroacetic acid was produced at a concentration of 4400 mg/L.

After tetrachloroethylene was mixed with the synthesized functional water and irradiated with light, it was found that trichloroacetic acidic aqueous solution was obtained in a yield of 87% in 60 minutes.

EXAMPLE 4

Preparation of Batch with Aerated Functional Water Gas

First, functional water with a pH value of 2.6, an oxidation-reduction potential of 1000 mV and a residual chlorine concentration of 75 mg/L was prepared, just like Example 1. 100 mL of this functional water was aerated with compressed air at a flow rate of 10 mL/min and the aerated functional water gas obtained was put in a 125 mL glass vial by the downwards displacement. Then the chlorine concentration in the glass vial was measured with an indicator tube (Gastec Service, Inc., No. 8H), and it was found that the concentration was about 200 ppm V.

8.2 µL (about 13 mg) of tetrachloroethylene stock solution was put in this glass vial, and the glass vial was sealed with a butyl rubber stopper with Teflon liner. Then this glass vial was irradiated with light, while stirring the solution, using a black light fluorescent lamp, just like Example 1.

After 60-minute light irradiation, the fluorescent lamp was turned off and the gas in the glass vial was measured; however no tetrachloroethylene was detected. Then water was put in the glass vial, so as to dissolve in the whole water the white crystal attached on its wall surface. The liquid was measured with a high pressure liquid chromatography; as a result, it was found that trichloroacetic acid was produced in an amount of 13 mg.

After tetrachloroethylene was mixed with the aerated functional water gas and irradiated with light, it was found that trichloroacetic acid was obtained in a yield of 99% in 60 minutes.

EXAMPLE 5

Continuous Production with Aerated Functional Water Gas

Trichloroacetic acid was produced continuously with an apparatus shown in FIGURE. First, 1000 mg/L of sodium chloride aqueous solution was put in a vial for electrolytic water provided for a strong acid electrolytic functional water production equipment (trade name: Oasis Bio Half; manufactured by Asahi Glass Engineering Co., Ltd.) and started to operate it, so as to produce electrolytic functional water continuously. The functional water obtained was measured in the same manner as in Example 1, and it was found that the functional water had a pH value of 2.4, an oxidation-reduction potential of 1000 mV and a residual chlorine concentration of 70 mg/L. This functional water was supplied continuously to a functional water aerating bath 1, so as to produce aerated functional water gas.

Then 2 g of tetrachloroethylene was put in the tetrachloroethylene vaporizing bath 2. The black light fluorescent lamp (trade name: FL10BLB; manufactured by Toshiba Corporation, 10 W), as the light irradiating means, which had been installed in the middle of the reaction coil made of the glass tube 20 mm in diameter and 1 m in length, was turned on previously, and after confirming the temperature of the reaction coil reached 60° C. or higher, compressed air was sent to the functional water aerating bath 1 and the tetrachloroethylene vaporizing bath 2, respectively, at a flow rate of 10 mL/min so as to aerate the functional water and the tetrachloroethylene via the respective bubblers. The chlorine concentration of the aerated functional water gas measured at this point was about 100 ppm V. And the tetrachloroethylene concentration measured with a gas chromatography was 900 ppm V. The aerated functional water gas and the gaseous tetrachloroethylene each obtained by the aeration were mixed with each other, then allowed to enter the reaction coil 4 from the upper end portion thereof, allowed to flow down while being subjected to light irradiation over about 30 minutes, and discharged from the lower end portion of the reaction coil 4. The liquid matter and solid matter were stored in the recovering bath 5 and the gas was discharged through a trap 6.

When bringing a glass rod with ammonium attached thereon close to the gas discharged from the recovering bath 5, white smoke was produced. On the other hand, when bringing a glass rod with ammonium attached thereon close to the gas discharged from the trap 6 which was filled with activated carbon and a sodium hydroxide aqueous solution, there occurred no changes. It is presumed from this fact that hydrogen chloride produced in the reaction coil 4 was not stored in the recovering bath 5, but discharged therefrom and removed by the adsorption in the trap 6.

In this experiment, the gas discharged form the recovering bath 5 was sampled with a gas tight syringe and measured with a gas chromatography. As a result, no tetrachloroethylene was detected.

All the tetrachloroethylene in the tetrachloroethylene vaporizing bath 2 was vaporized in about 30 minutes. After that, compressed air was sent for another 30 minutes, then sending compressed air was stopped and the fluorescent lamp was turned off. The white crystallized matter attached on the bottom portion and the wall portion of the recovering bath 5 was washed off and recovered, and then subjected to a high pressure liquid chromatography. The measurement showed that 1.5 g of trichloroacetic acid was produced. There were observed no peaks of other products.

The results showed that trichloroacetic acid could be produced continuously in the average yield of 78% when using the apparatus shown in figure and mixing tetrachloroethylene with functional water and irradiating the mixture with light in its reaction coil for 30 minutes.

What is claimed is:

1. An apparatus for preparing solid trichloroacetic acid comprising:

a reaction coil for reacting a mixed gas comprising gaseous tetrachloroethylene and a gas produced by aerating a functional water with an oxygen-containing gas, said reaction coil being capable of producing said trichloroacetic acid under light irradiation;

a light irradiator, about which the reaction coil is wound, for irradiating the mixed gas in the reaction coil with light in a wavelength range of 300 to 500 nm to decompose tetrachloroethylene and generate said trichloroacetic acid; and a recovery bath connected to the reaction coil for extracting said trichloroacetic acid from the reacted mixed gas, having an inlet and an outlet, wherein the inlet is located in an upper portion of the recovery bath for depositing said trichloroacetic acid in a liquid state on a bottom of the recovery bath, in which said trichloroacetic acid can be cooled and condensed, wherein the outlet is located in the upper portion of the recovery bath for exhausting the mixed gas from which said trichloroacetic acid has been extracted, and wherein the apparatus further comprises a trap, connected to the recovery bath, for adsorbing excess chlorine gas and hydrogen chloride gas from the mixed gas, which has already undergone the trichloroacetic acid extraction.

2. The apparatus according to claim 1, further comprising a source of said gas produced by aerating the functional water with the oxygen-containing gas.

3. The apparatus according to claim 1, further comprising a source of said vaporized tetrachloroethylene.

4. The apparatus of claim 2, wherein said source of said gas produced by aerating the functional water with the oxygen-containing gas comprises a functional water aerating bath.

5. The apparatus according to claim 3, wherein the source of said vaporized tetrachloroethylene comprises a tetrachloroethylene vaporizing bath.

6. The apparatus according to claim 3, wherein the source of said vaporized tetrachloroethylene comprises a bubbler.

7. The apparatus according to claim 1, wherein the light irradiator emits light in a wavelength range of 350 to 450 nm.

8. The apparatus according to claim 1, wherein the light irradiator provides light having an irradiation dose in a range of 10 $\mu$W/cm$^2$ to 10 mW/cm$^2$.

9. The apparatus according to claim 8, wherein the light irradiator provides light having an irradiation dose in a range of 50 $\mu$W/cm$^2$ to 5 mW/cm$^2$.

10. The apparatus according to claim 1, wherein said source of said gas produced by aerating the functional water with oxygen-containing gas provides a gas with a chlorine concentration of 5 to 1000 ppmV.

11. The apparatus according to claim 10, wherein the chlorine concentration is 20 to 500 ppmV.

12. The apparatus according to claim 1, wherein the light irradiator irradiates light and heats the mixed gas such that said trichloroacetic acid generated in the reaction coil is kept in a liquid state.

* * * * *

UNITED STATES PATENT AND TRADEMARK OFFICE
CERTIFICATE OF CORRECTION

PATENT NO. : 6,800,257 B1
DATED : October 5, 2004
INVENTOR(S) : Akira Kuriyama et al.

It is certified that error appears in the above-identified patent and that said Letters Patent is hereby corrected as shown below:

<u>Title page, Item [54] Column 1, line 2,</u>
Title, "TRICHLORACETIC" should read -- TRICHLOROACETIC --.

<u>Title page,</u>
Item [56], References Cited, FOREIGN PATENT DOCUMENTS
"02000084357" should read -- 2000-84357 --.

Signed and Sealed this

Twenty-second Day of February, 2005

JON W. DUDAS
*Director of the United States Patent and Trademark Office*